United States Patent [19]

Heisler et al.

[11] Patent Number: 5,766,199
[45] Date of Patent: Jun. 16, 1998

[54] ENDOSCOPIC SHAVER BLADE WITH RESILIENT CUTTING EDGES

[75] Inventors: Gary R. Heisler, Holiday; Robert A. Van Wyk, Largo, both of Fla.

[73] Assignee: Linvatec Corporation, Largo, Fla.

[21] Appl. No.: 631,714

[22] Filed: Apr. 10, 1996

[51] Int. Cl.[6] .................................................. A61B 17/14
[52] U.S. Cl. ......................................... 606/180; 606/170
[58] Field of Search ................................. 606/180, 170, 606/171, 167; 128/751; 604/22

[56] References Cited

U.S. PATENT DOCUMENTS

| | | |
|---|---|---|
| 3,732,858 | 5/1973 | Banko . |
| 3,844,272 | 10/1974 | Banko . |
| 3,882,872 | 5/1975 | Douvas et al. . |
| 3,945,375 | 3/1976 | Banko . |
| 4,167,943 | 9/1979 | Banko . |
| 4,274,414 | 6/1981 | Johnson et al. . |
| 4,620,547 | 11/1986 | Boebel . |
| 4,649,919 | 3/1987 | Thimsen et al. . |
| 4,834,729 | 5/1989 | Sjostrom . |
| 4,844,088 | 7/1989 | Kambin . |
| 4,850,354 | 7/1989 | Mcgurk-Burleson . |
| 5,007,917 | 4/1991 | Evans . |
| 5,112,299 | 5/1992 | Pascaloff . |
| 5,123,904 | 6/1992 | Shimomura et al. ............... 604/22 |
| 5,423,844 | 6/1995 | Miller . |
| 5,437,630 | 8/1995 | Daniel et al. ................... 606/170 |
| 5,489,291 | 2/1996 | Wiley . |

FOREIGN PATENT DOCUMENTS

WO 89/02250  3/1989  WIPO .

Primary Examiner—Michael Powell Buiz
Assistant Examiner—Kevin Truong
Attorney, Agent, or Firm—Gene Warzecha

[57] ABSTRACT

A rotating endoscopic shaver blade assembly adapted for side-cutting and end-cutting. A pair of longitudinally extending, symmetrical fingers extends from the distal end of an elongated tubular inner member and are juxtaposed adjacent a window at the distal end of an elongated tubular outer member. Each of the fingers is provided with laterally facing and transversely facing cutting edges and has a curvilinear profile terminating at a distal tip. The distal tips of the fingers are separated by an axially aligned gap which enables limited stress-relieving radial movement of the fingers.

7 Claims, 7 Drawing Sheets

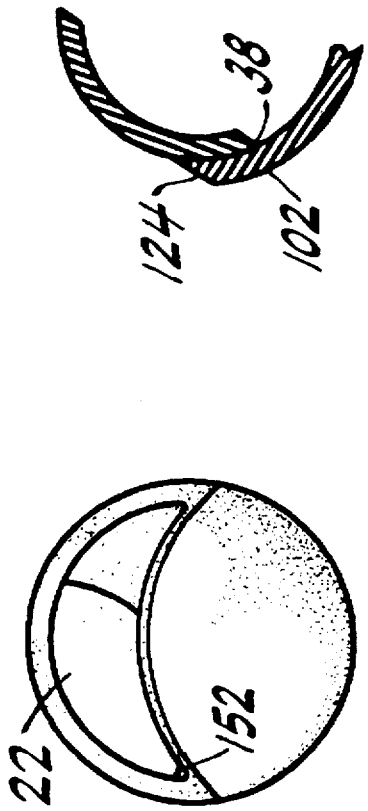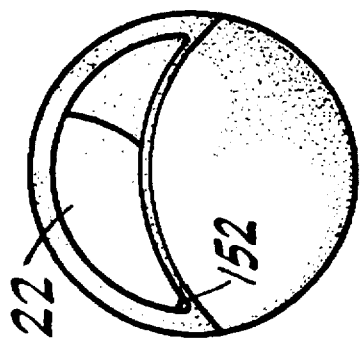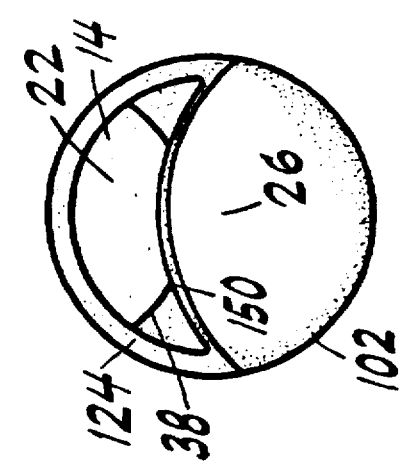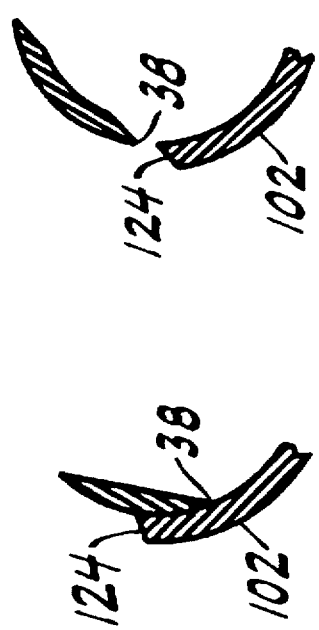
FIG. 19
FIG. 20
FIG. 18
FIG. 16
FIG. 21
FIG. 22

ENDOSCOPIC SHAVER BLADE WITH RESILIENT CUTTING EDGES

BACKGROUND OF THE INVENTION

1. Field of the Invention

The invention relates to elongated, powered surgical instruments for use in endoscopic tissue resection. More particularly, the invention relates to an instrument having an elongated inner tube rotatably situated within an elongated stationary outer tube, both inner and outer tubes having cutting apertures at their distal ends which cooperate to resect or otherwise affect tissue during endoscopic surgical procedures.

2. Description of the Prior Art

The use of elongated surgical cutting or resection instruments has become well accepted in performing closed surgery such as arthroscopic or, more generally, endoscopic surgery. In closed surgery, access to the surgical site is gained via one or more portals, and instruments used in the surgical procedure must be elongated to permit the distal ends of the instruments to reach the surgical site. Surgical cutting instruments for use in closed surgery—also known as "shavers"—conventionally have a straight, elongated outer tubular member terminating at a distal end having an opening in the end or side wall (or both) to form a cutting port or window and a straight, elongated inner tubular member concentrically disposed in the outer tubular member and having a distal end disposed adjacent the opening in the distal end of the outer tubular member. The distal end of the inner tubular member also has a window opening having a surface or edge for engaging tissue via the opening in the outer tubular member and in many cases (but not all) cooperates with the outer opening to shear, cut or trim tissue. In some cases, such as burrs, the opening in the outer tube merely allows access to the tissue and does not otherwise cooperate with the inner window. The inner tubular member is rotatably driven about its axis from its proximal end, normally via a handpiece having a small electric motor which is controlled by finger actuated switches on the handpiece, a foot switch or switches on a console supplying power to the handpiece. The distal end of the inner tubular member can have various configurations depending upon the surgical procedure to be performed, and the opening in the distal end of the outer tubular member has a configuration to cooperate with the particular configuration of the distal end of the inner tubular member. The various configurations and combinations of inner and outer members produce assemblies, the individual and combined components of which are referred to generically as shaver blades or cutting blades. Resected tissue is aspirated through the hollow lumen of the inner tubular member to be collected via a vacuum tube communicating with the handpiece.

The aforementioned elongated surgical cutting instruments have also been produced in angled configurations in which the distal tips of the inner and outer members are aligned and offset or bent at either a fixed or variable angle from the proximal ends of the aligned inner and outer members. Examples of fixed and variable angle rotary surgical instruments are shown in U.S. Pat. Nos. 4,646,738 (Trott) and 5,411,514 (Fucci et al.), both assigned to the assignee hereof, and incorporated by reference herein. In other respects the operation of fixed and variable angle shavers is largely the same as that of the straight shavers described above.

Shaver blades are usually optimized for a particular surgical procedure or part thereof. Thus, during a procedure a surgeon may use shaver blades optimized for cutting soft tissue. If during the procedure it is necessary to resect harder tissue such as bone, the surgeon may either try to use the blade already in use or may switch to a shaver in the form of a burr or more aggressive blade. Usually the latter approach is chosen since the soft tissue blade will clog or lock-up when resecting bone. Cutting edges at the distal end of the inner tube cutting window do not have the low included angle geometry required for efficient bone resection. The high forces encountered when resecting bone tend to cause blade failure through deformation due to high torsional loads.

It would, therefore, be desirable and it is an object of this invention to produce a universal shaver blade more suitable for all types of tissue than prior art devices.

Additionally, it has been difficult to produce a practical design suitable for both side and end cutting while maintaining blade sharpness and strength. Consequently, prior art shaver blades are most often configured to produce one or the other, but usually not both. Side cutting shavers have side and end facing windows in the cylindrical wall of the outer member and the cutting edge on the inner member is designed to affect resection along the outer window rim which is on a line generally parallel or slightly inclined to the shaver axis. The term "side cutting" includes full radius resection instruments in which the plane of the outer window is angled relative to the axis. While the side facing cutters have windows which are partially end facing, they are not efficient as end cutters because the cutting edges at the distal ends of the inner and outer tube cutting windows both have large included angles. That is, the edge is not sharp enough so that resection at the distal end of the cutting window is accomplished essentially by a "pinching" action between the relatively flat inner tube edge and outer tube cutting edges passing by each other. Similarly, cutting instruments designed for end cutting are relatively inefficient as side cutters because the cutting edges at the sides of the inner and outer tube cutting windows both have large included angles. Tissue is resected in this region by the same "pinching" mechanism referred to previously. In certain cases resection efficiency has been somewhat improved by decreasing the wall thickness of the inner tube (thus making the flat edge narrower), the outer tube or both, either throughout the tube length or at the distal end radius only. Such tubes are, however, prone to deformation due to high torsional loads when the inner and outer cutting edges encounter tissues which are difficult to resect. Such deformation often results in lock-up of the shaver or metallic debris at the work site due to interference between inner tube and outer tube cutting edges.

A common goal of shaver blade production is sharpness. However, while this goal may be achieved in a variety of ways, to be truly practical the design of the blade and its method of manufacture must be adaptable to efficiently produce large volumes of shaver blades with sharp edges.

A known design (FIGS. 1–4) for improving blade efficiency is a shaver blade assembly having an outer window lying in a plane inclined to the blade axis (FIG. 1) and a dual-window inner member having inwardly facing cutting teeth (FIG. 2). The planar form of the outer window produces a teardrop window shape having a low included angle around the window periphery, although this angle is not uniform around the periphery. The dual-window form of the inner may be created by, for example, a wire EDM (electrical discharge machining) process in which the wire is passed transversely to the axis through diametrically opposed portions of the cylindrical wall of the inner member. The intersection of the cylindrical outer surface and the inwardly facing wall surface thus created defines the cutting edge. It will be understood that passing the wire through the opposed walls while keeping the wire at large radial distances from the tube axis can produce the scalloped pattern of parallel cutting edges shown in FIG. 2. As seen in FIG. 4, diametrically opposed windows are formed by shaping diametrically opposed sides of the inner member. The radially outermost edges of the periphery of the windows thus formed in the surface of the inner tube intersect with the cylindrical surface of the tube to form the longitudinally extending inner cutting edges with teeth. These edges have an included angle which decreases as the distance between the edge and the tube axis increases. The sharper this edge, the easier it is to cut tissue as these inner cutting edges rotate past the outer window periphery.

While the shaver blade described above is effective, the inner window formation limits the efficiency of the tissue resection at the distal tip and does little to enable the blade to resect hard tissue such as bone. The wall thickness at the distal tip of the outer enables the inner cutting edge to cut only tissue which can extend past this thickness and into the outer window. Because of the need or desire for a bearing contact between the distal tips of the inner and outer members (on the axis along the inner surface) and because of the rounded tip of the inner, this design is limited in its ability to do end cutting. For example, as shown in FIGS. 3 and 4, the distal tip of the prior art dual-window inner member is cut flat and is spaced from the axis. Moreover, the manufacture of a tip such as this is possibly more difficult than one would desire in a production environment.

It is accordingly an object of this invention to produce a rotating shaver blade capable of use as a side cutter and/or end cutter.

It is also an object of this invention to produce a rotating shaver blade in which the inner member has a dual cutting window configuration.

It is an additional object of this invention to produce a rotating shaver blade utilizing an inwardly facing portion of the cylindrical wall of an elongated tube to provide a cutting edge.

It is also an object of this invention to produce a rotating shaver blade capable of resecting soft tissue or hard tissue such as bone.

It is another object of this invention to produce an inner member for a shaver blade assembly, the inner member having a plurality of cutting edges at its distal tip and the cutting edges having low included angles.

It is also an object of this invention to produce such a shaver blade suitable for fixed and bendable shavers.

It is also an object of this invention to produce such a shaver blade which has a minimized tendency to seize or produce debris due to deformation of the inner or outer tube during use.

It is a further object of this invention to produce a shaver blade having a cutting edge which is resilient enough to flex in a stress-relieving manner when exposed to excessive resecting forces, thus minimizing any tendency to seize.

SUMMARY OF THE INVENTION

These and other objects of this invention are achieved by the preferred embodiment disclosed herein which is a surgical tissue resecting instrument comprising an elongated outer tubular member, having an axis, a distal end, a proximal end and an opening at the distal end and an elongated inner tubular member axially aligned within and adapted to move within the outer tubular member. The inner member has a cylindrical body with a distal end, a proximal end and a cutting means at the distal end for cutting tissue presented through the opening of the outer member. The cutting means comprises at least two diametrically opposed finger members extending longitudinally from the distal end of the inner tubular member, each of the finger members comprising a body having a proximal portion and a distal portion. The proximal portion of the fingers is longitudinally extending and joined to the cylindrical body of the inner tubular member. In the preferred embodiment this proximal portion subtends a predetermined arcuate distance of less than 180° and the distal portion is joined to the proximal portion. The distal portion transversely and longitudinally extends from the proximal portion and terminates at a point spaced a predetermined distance from the axis. Consequently, the distal tips of the fingers are spaced from each other thus enabling the fingers to flex radially in response to excessive forces to which they may be subjected during tissue resection.

In another aspect the invention is the method of forming a shaver blade from an elongated cylindrical tube having an axis, a predetermined outer diameter and a closed, rounded end. The method comprises the steps of shaping the distal tip of the tube by providing a shaping means for shaping the closed, rounded end of the tube. In a preferred embodiment, the shaping means has a length greater than the tube's diameter, a width less than the tube's diameter and the method further comprises the step of shaping the distal tip of the tube by aligning the shaping means transversely to the axis of the tube and passing it axially through the distal tip of the tube. The shaping means is then moved proximally along a first predetermined contour, to a proximal area on the tube, and then along a second predetermined contour, symmetrical to the first predetermined contour, back to the point of entry.

In yet another aspect, the invention is the method of resecting tissue with a surgical shaver blade assembly having an elongated inner tubular member rotatably situated within an elongated outer tubular member. This method comprises the steps of providing a window at the distal end of the outer tubular member and providing at least one pair of diametrically opposed fingers at the distal end of the inner tubular member, the fingers having laterally facing cutting edges. The method further comprises the steps of rotating the inner tubular member relative to the outer to resect tissue and enabling the fingers to flex radially in response to forces imposed on them during resection.

BRIEF DESCRIPTION OF THE DRAWINGS

FIG. 16 is an end view of FIG. 15.

FIG. 18 is an end view of FIG. 17.

FIG. 19 is a sectional view of FIG. 17 taken along the line 19—19.

FIG. 20 is a sectional view of FIG. 17 taken along the line 20—20.

FIG. 21 is a sectional view of FIG. 17 taken along the line 21—21.

FIG. 22 is a sectional view of FIG. 17 taken along the line 22—22.

DESCRIPTION OF THE PREFERRED EMBODIMENT

Figure 1:
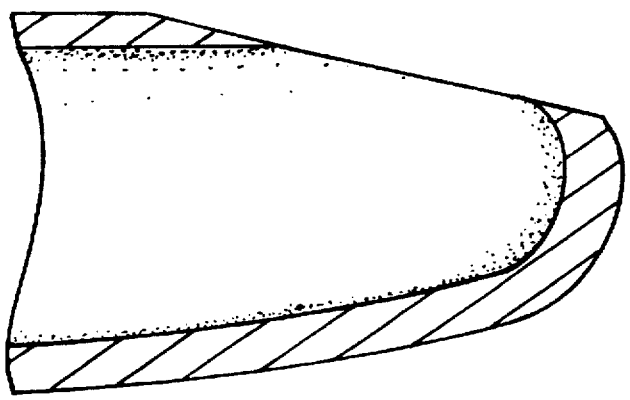
FIG. 1 is a cross-sectional view of the distal tip of an outer member of a prior art shaver blade assembly.
Figure 2:
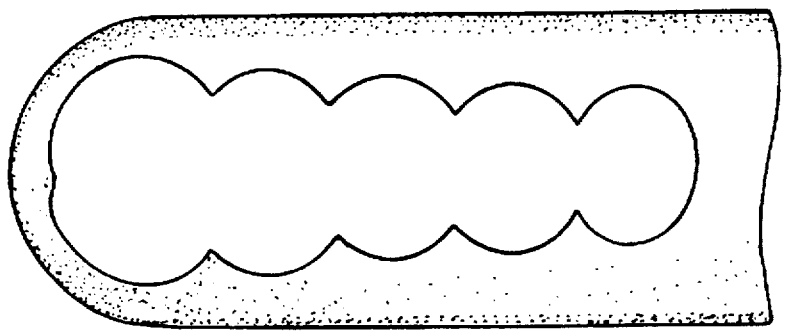
FIG. 2 is a plan view of a dual-window inner member for use with the outer member shown in FIG. 1.
Figure 3:
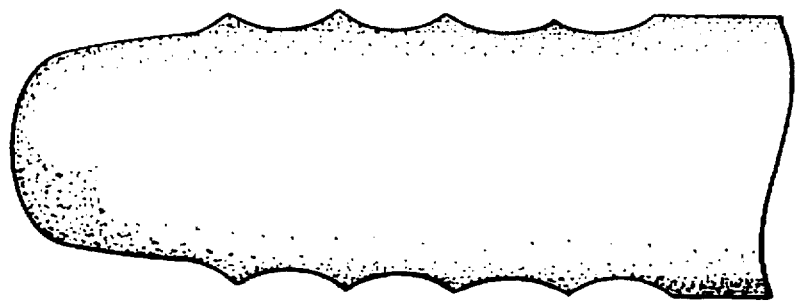
FIG. 3 is a side elevational view of FIG. 2.
Figure 4:
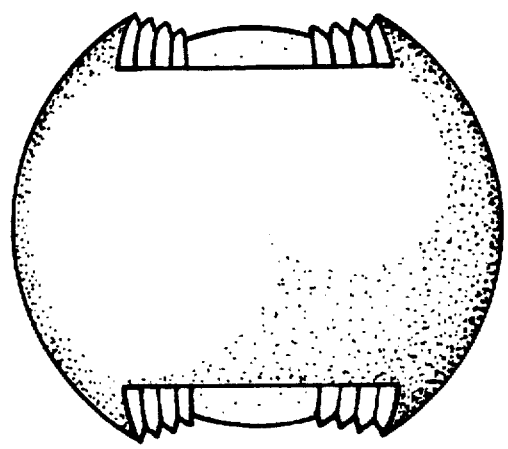
FIG. 4 is an end view of FIG. 3.
Figure 5:
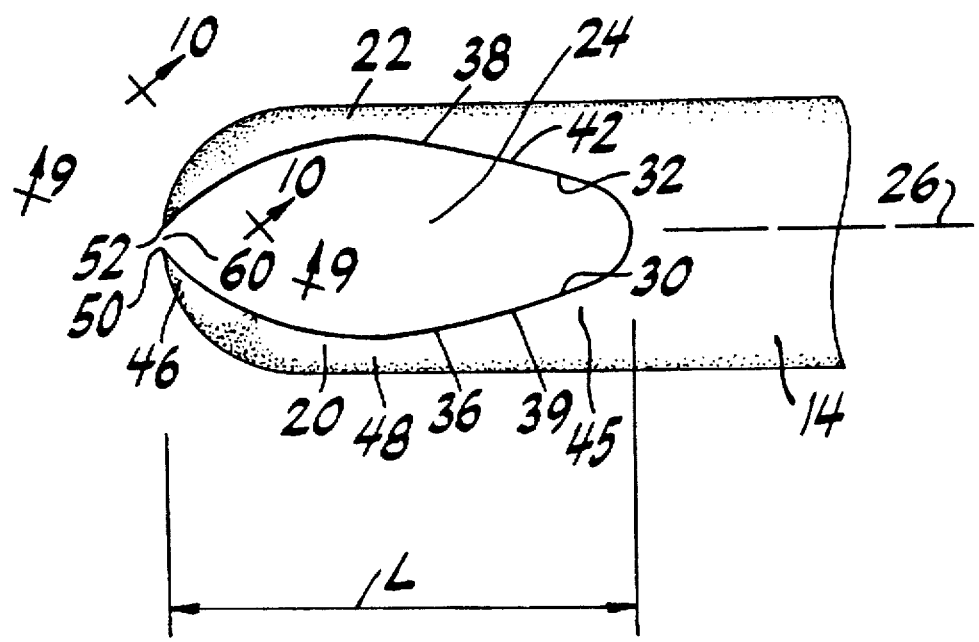
FIG. 5 is a plan view of the distal tip of an inner member of a shaver blade assembly constructed in accordance with the principles of this invention.
Figure 6:
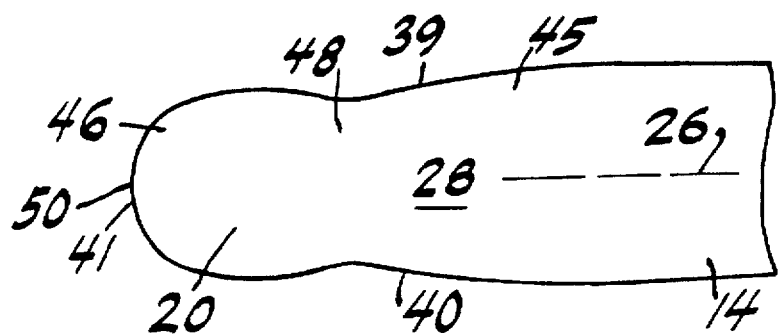
FIG. 6 is a side elevational view of FIG. 5.

A detailed view of the distal tip of an inner member 14, constructed in accordance with the principles of this invention, is shown in FIGS. 5 through 8. It will be understood that the blade is shown removed from an associated outer tube with which it must be assembled to produce a shaver blade assembly for proper use. The distal tip of inner member 14 is provided with a pair of diametrically opposed, transversely arcuate fingers 20 and 22 which define an open, side and end-facing space 24 between them. Fingers 20 and 22 are symmetrical about axis 26 and are, in the preferred embodiment, integrally formed with the cylindrical body of inner member 14 and extend from the body a length L. Because of their symmetrical nature, references to one finger herein will be understood to apply to the other. The outer surface 28 of each finger is an arcuate continuation of the cylindrical outer surface of the inner member. Similarly, the inner surface 29 of each finger is an arcuate continuation of the inner surface of the inner member. The radially inwardly facing surfaces 30 and 32 of fingers 20 and 22, respectively, are also symmetrical and face each other across an imaginary axial plane intersecting axis 26. Surfaces 30 and 32 abut each other on the axis at the proximal end of space 24 and form, in effect, one continuous surface around the space although for ease of explanation it is assumed herein that each finger has a separate surface. The intersection of these surfaces 30 and 32 with the external cylindrical surface 34 of the inner member defines cutting edges 36 and 38, respectively. Each edge 36 and 38 has a curvilinear U-shaped profile (when viewed laterally as in FIG. 6) having a pair of longitudinally extending edges, the distal ends of which are joined by a transversely and longitudinally extending distal edge. Thus, as best seen in FIG. 6, finger 20 carries a top longitudinal edge 39, a bottom longitudinal edge 40 and a distal edge 41. Similarly, finger 22 carries a top longitudinal edge 42, a bottom longitudinal edge 43 and a distal edge 44. The longitudinal edges lie along the proximal, side-facing portion of each finger body while the distal edges lie along the end-facing, distal portion of the body. While the longitudinal edges generally face laterally to the axis to resect tissue as the blade rotates, the distal edges have a transversely facing component near the axis to resect tissue as the blade is axially pushed against it. As will be understood below, the distal edges are separated from each other by a distal end slot 60.

Figure 10:
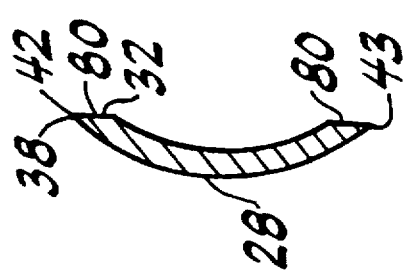
FIG. 10 is a sectional view of FIG. 5 taken along the line 10—10.
Figure 13:
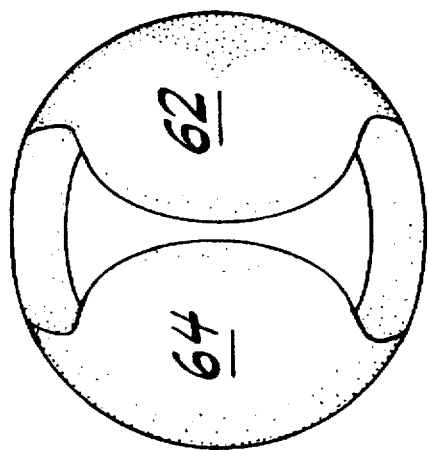
FIG. 13 is an end view of FIG. 12.
Figure 9:
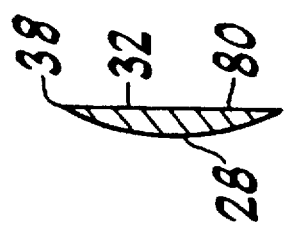
FIG. 9 is a sectional view of FIG. 5 taken along the line 9—9.
Figure 11:
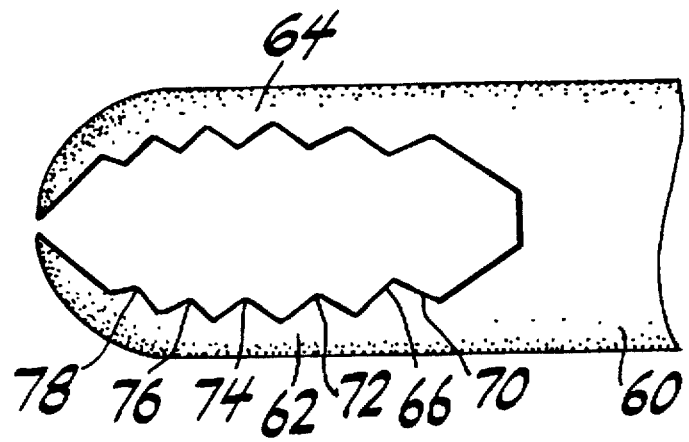
FIG. 11 is a plan view of an alternate embodiment of the invention.
Figure 12:
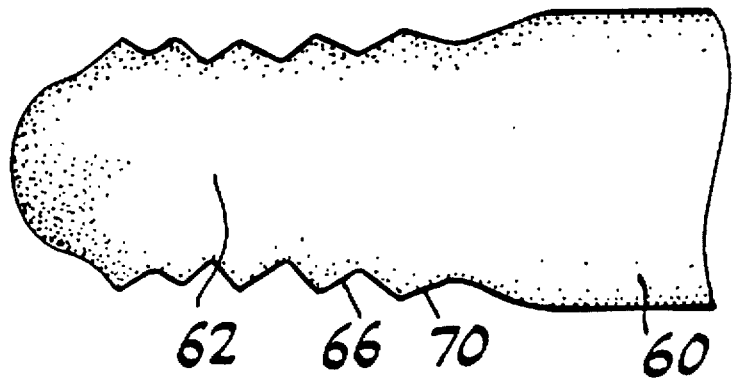
FIG. 12 is a side elevational view of FIG. 11.

The contour of edges 36 and 38 is such that the included angle varies along their lengths and gets smaller at the distal tip. It will be understood that because of the dual-window configuration, as the inner blade rotates within the outer, only one finger and one of its corresponding edges will be active to resect tissue at any one time. Each finger has a proximal end 45 and a distal end 46 and each part of the fingers subtends a different arcuate distance relative to axis 26 depending upon its position along the length of inner blade 14 (as seen in FIGS. 9 and 10). Thus, in a plane transverse to the axis, the arcuate distance subtended by the proximal portion 45 is greater than that subtended by an intermediate portion 48. As best seen in FIG. 6, each finger has a contoured pinching "hour glass" profile having its most narrow portions at area 48 and adjacent the distal tips 50 and 52 of the fingers. The large size of the proximal portion 45 provides strength and support for the relatively smaller distal tip.

Figure 7:
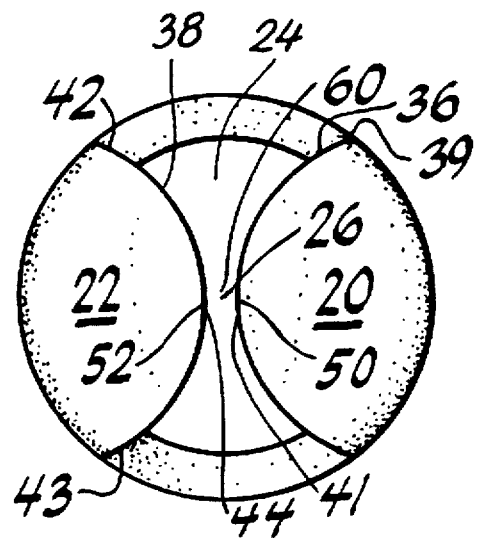
FIG. 7 is an end view of FIG. 6.
Figure 8:
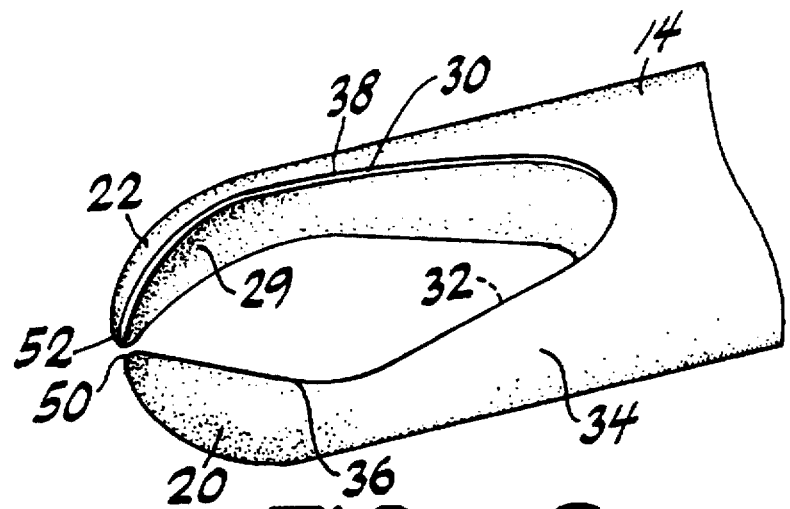
FIG. 8 is a front perspective view of FIG. 7.

The invention includes the method of shaping a cylindrical tube to form a shaver blade. It will be understood that each finger 20, 22 may be formed at the distal tip of an inner tube having a closed, rounded end. While a variety of shaping means may be used, in the preferred embodiment a shaping means such as a wire-like member is used in the form of a wire EDM (electrical discharge machining) process or the like. In such a process the wire follows a predetermined contour (preferably programmed on a computer numerical control (CNC) machine) through diametrically opposed cylindrical wall portions of blade 14 in a direction transverse to axis 26 and perpendicular to the plane of FIG. 5. This enables a single wire to simultaneously form finger 20 and both of its longitudinal edges 39 and 40 and its distal edge 41, as best seen in FIG. 7. Continuing motion of the wire can simultaneously produce edges 42, 43 and 44 on finger 22. The intersection of the cylindrical wall of the inner member 14 with the wire creates surfaces 30 and 32 within the thickness of the wall and the intersection of these surfaces with the outer cylindrical surface of inner member 14 defines the included angle without any additional machining operation. As seen in sectional views of FIGS. 9 and 10, the body of each finger has at its opposite sides an included angle which varies depending upon the particular position on the finger at which the measurement is taken. Also, because of the generally hemispherical shape of the outer surface of the distal tip of the inner member 14, the finger formation process produces curved, sharpened distal edges 41 and 44, best seen in FIG. 7. It is noted that these distal edges of each finger are tapered to a point as viewed in FIG. 5, thus creating a sharper edge for endwise resection. All points of surfaces 30 and 32 lie in a common contour 80 which may have a variety of profiles when viewed as a projection on a plane normal to the axial plane between the fingers. In the preferred embodiment, contour 80 follows the curvilinear shape of space 24 defined by surfaces 30 and 32 as shown in FIGS. 5, 7 and 8. While in the preferred embodiment all the points in the surfaces lie on contour 80, it will be understood that the shape of surfaces 30 and 32 could be varied to be contoured, i.e. something other than parallel to the axial plane.

Figure 14:
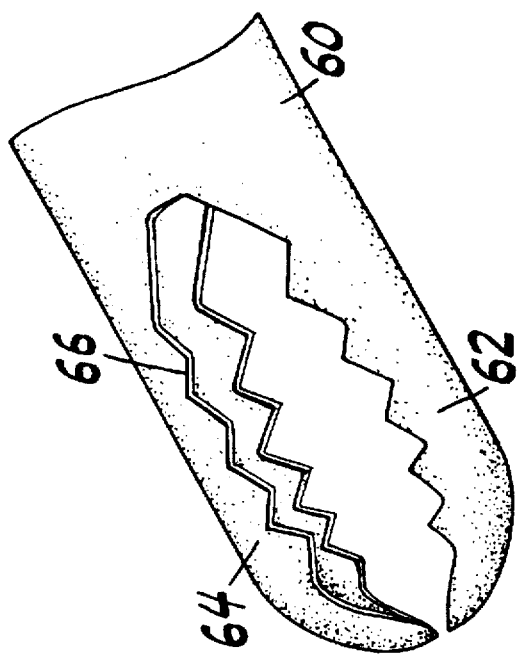
FIG. 14 is a front perspective view of FIG. 13.

The dual-window structure of inner member 14 may be thought of as having one window above axis 26 as viewed in FIGS. 6 and 7 and another window below the axis. The curvilinear window periphery has edges of differing included angles. Producing the cutting windows by machining the cylindrical inner tube through both walls of the inner tubular member from a point between the axis and the tube wall, and at a relatively large distance from the axial plane, produces low included angle cutting edges at the intersection of the opening with the tube side-wall and distal tip outer surfaces. The cutting windows are joined at the distal tip thereby producing a distal end slot 60 having adjacent finger ends with low included angle cutting edges (best seen in FIGS. 5 and 9). Since the inner tube is sized to be rotatably received within an outer tube with little annular clearance (shown in FIG. 15), the creation of distal slot 60 does not adversely affect shaver blade performance. While there is no axial bearing contact between the inner and outer members, the area around distal tips 50 and 52 is transversely extending and sufficiently large to provide adequate bearing contact between the inner and outer members. As best seen in the end view shown in FIGS. 14 and 15, the inner and outer members 102 and 14 overlap in the area of axis 26 in order to create a bearing contact area along a predetermined part of the proximally facing inner surface of the outer member and the transversely extending outer surface of the inner member.

Rotation of the inner tubular member relative to the outer tubular member, as will be understood below, causes tissue resection through a shearing or scissoring action as the cutting edges of the inner and outer windows are brought into proximity. The low included angle of the periphery of the fingers and the distal end slot 60 cooperate to produce efficient endwise tissue resection allowing use of a single shaver for end cutting, side cutting and resection of bone as well as soft tissue. An excessive increase in cutting forces due to tissue toughness or dulling of the cutting edges which may cause prior art inner tubes to seize wills because of the resiliency of the fingers and distal end slot 60, cause the fingers to flex radially inwardly away from the interior of the outer tube thereby preventing interference between the distal ends of the inner tube and outer tubes and enabling continued rotation of the inner tube.

In certain cases, as when cutting extremely soft or resilient tissue, resection may be difficult because the scissoring action referred to above may tend to eject the tissue from the cutting windows. An alternative embodiment of the distal tip of an inner member 60 is shown in FIGS. 11 through 14 to minimize this. Inner member 60 is identical to inner member 14 except that the fingers 62 and 64 are provided with teeth 66 along portions of their periphery. Furthermore, while the teeth along finger 62 are symmetrical to their counterparts on finger 64, the profile of the teeth varies as a function of their longitudinal position. Thus, referring for simplicity to only the teeth on one edge of finger 62, the proximal-most tooth 70 has a wider base than adjacent tooth 72 and the bases of teeth 74, 76 and 78 get progressively narrower toward the distal tip. The teeth may be irregularly shaped along the rim of the cutting edge in order to optimize the tip rake angle and root rake angle at each tooth position. Since each tooth varies in lateral position from the center line, the previously discussed wire EDM formation process easily produces varying included angles in different teeth.

Figure 15:
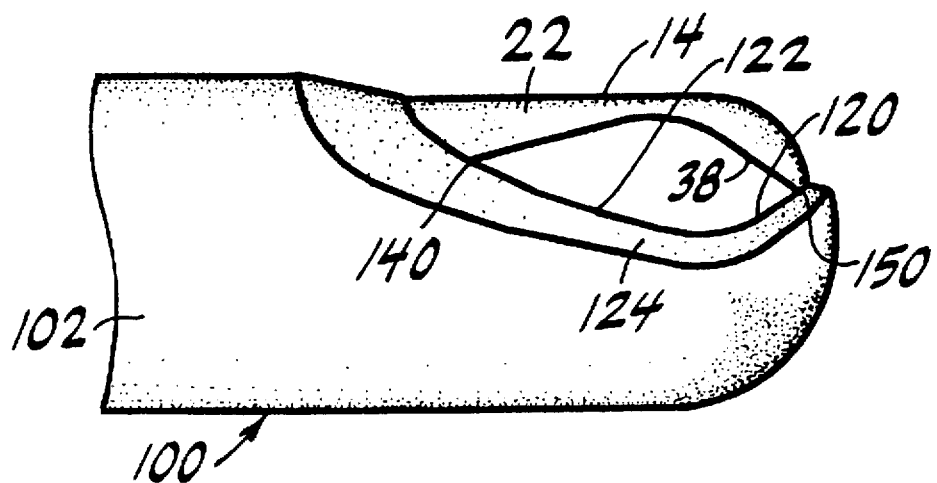
FIG. 15 is a view of the distal tip of a shaver blade assembly formed by the combination of the inner member shown in FIGS. 5 through 8 assembled with a representative outer member.

The use of the invention is explained by reference to FIG. 15 showing the distal tip of a shaver blade assembly 100 comprising an elongated outer tube 102 assembled with an elongated inner tube 14 rotatably situated within its interior and more particularly described in FIGS. 5 through 8. The proximal ends of the inner and outer tubes are conventional and do not form any part of this invention. A representative description of the proximal ends of shaver blade assembly 10 may be had by reference to U.S. Pat. No. 5,411,514 (Fucci et al.), assigned to the assignee hereof and incorporated by reference herein. Outer tube 102 is provided at its distal end with a window 120 having a peripheral edge 122 entirely surrounded by an angled land surface 124. The edge of outer window 120 is considered sharpened since land 124 lies at an angle A relative to the axis 126 of the tube as more particularly described in a co-pending patent application directed to this particular structure, assigned to the assignee hereof and incorporated by reference herein.

Figure 17:
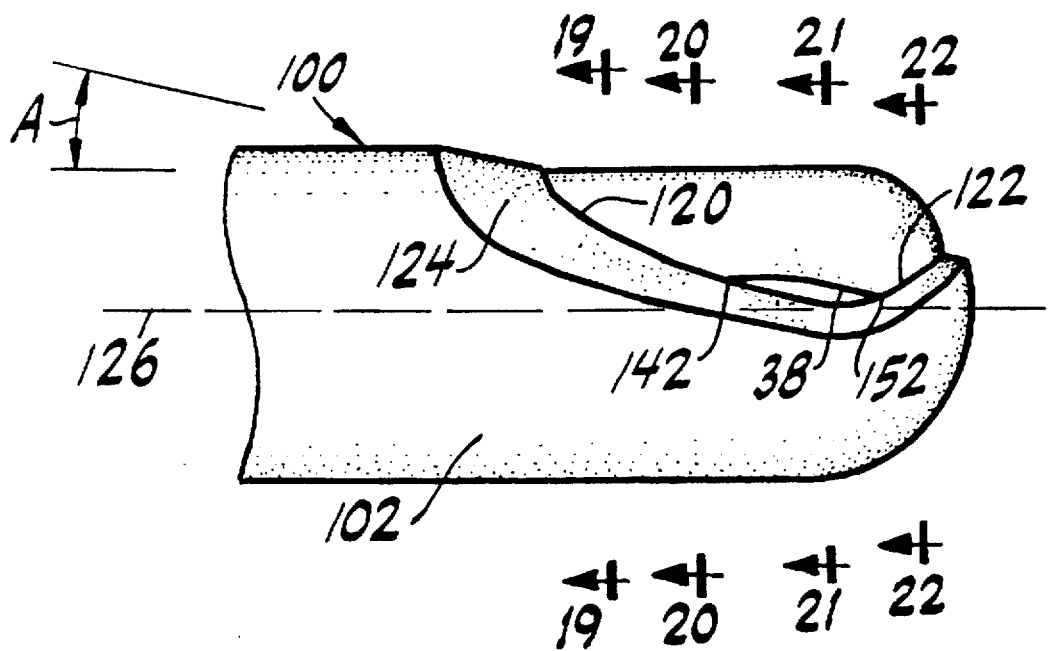
FIG. 17 is a view of FIG. 15 showing the position of the components in a different stage of operation.

It will also be noted that the cutting windows of the inner member face not only endwise as shown in FIG. 16 but laterally as shown in FIG. 15. That is, at any given point during the rotary motion of the inner member in a given direction the particular inner edge which is active at the time, for example edge 38, will intersect the outer edge 122 at two points: a point 140 along the laterally facing portion of window 20 (FIG. 15) and a point 150 along the end facing portion of the blade as shown in FIG. 16. The trailing edge will be understood to be inactive since it will face in a direction opposite to the direction of rotation. Furthermore, the active edge will intersect outer edge 122 of the outer member at varying angles depending upon the position of the inner member. Thus, as shown in FIG. 15, at a given point in time edge 38 intersects edge 122 at points 140 and 150 while at a subsequent time, as the inner member rotates within the outer member, edge 38 intersects edge 122 at points 142 and 152 shown in FIG. 17. The angles between the edges at these points vary and the variation in this angle of attack facilitates the cooperative shearing action of the two cutting edges 38 and 122 along the periphery of outer window 120.

A representative set of cross-sections of the inner and outer windows is shown in FIGS. 19 through 22. The various views are taken along the respectively numbered lines in FIG. 17, although only the portions of the tubes immediately adjacent the edges are shown. It will be noted that the included angles of inner and outer edges at the points represented by FIGS. 19 and 20 are relatively sharp although the sharpness is greater at the point represented by FIG. 21. The point represented by FIG. 22 is approximately the same as point 150, thus demonstrating that the present invention provides a device capable of sharp edges on end facing cuts.

While the preferred embodiment disclosed herein utilizes two diametrically opposed fingers, a greater number of fingers could easily be utilized within the scope of the invention. Additionally, the fingers may be formed separately from the body of the inner member and subsequently attached. Also, the fingers need not necessarily have arcuate outer surfaces aligned with the cylindrical outer surface of the inner member. Another configuration may employ a rotatable shaft having affixed to one end a cutting tip in the form of the fingers.

It will be understood by those skilled in the art that numerous improvements and modifications may be made to the preferred embodiment of the invention disclosed herein without departing from the spirit and scope thereof.

What is claimed is:

1. A method of resecting tissue with a surgical shaver blade assembly comprising an elongated inner tubular member having an axis and rotatably situated within an elongated outer tubular member, said method comprising the steps of:

providing a window at a distal end of said outer tubular member;

providing at least one pair of diametrically opposed, longitudinally extending finger members at a distal end of said inner tubular member, each of said finger members having a distal tip and a periphery provided with laterally and longitudinally facing cutting edged;

rotating said inner tubular member relative to said outer tubular member to resect tissue presented through said window; and enabling said finger members to flex radially in response to forces imposed on said finger members during resection.

2. A method according to claim 1 wherein said window is at least partially end-facing and further comprising the step of providing on at least one of said finger members a transversely facing cutting edge in sliding engagement with the distal end of said outer tubular member for resecting tissue presented axially into said window.

3. A method according to claim 1 further comprising the step of forming said distal tip of at least one of said finger members so that it extends both transversely and longitudinally.

4. A method according to claim 3 wherein said step of enabling flexing of said finger members is facilitated by providing a predetermined gap between said distal tips of said longitudinally extending finger members.

5. A method according to claim 3 wherein a portion of said periphery is curvilinear along at least said laterally facing cutting edge.

6. A method according to claim 3 wherein a portion of said periphery is curvilinear within a plane perpendicular to an axial plane passing through the axis of said inner tubular member.

7. A method according to claim 1 wherein each of said finger members has a distal end and a proximal end, further comprising the step of:

providing a first predetermined transverse spacing between said finger members at their proximal ends and a second predetermined transverse spacing between said finger members at their distal ends, said second predetermined transverse spacing being less than said first predetermined transverse spacing.

\* \* \* \* \*